US010645307B2

United States Patent
Amano et al.

(10) Patent No.: US 10,645,307 B2
(45) Date of Patent: May 5, 2020

(54) ENDOSCOPE APPARATUS

(71) Applicant: Sony Olympus Medical Solutions Inc., Tokyo (JP)

(72) Inventors: Kohtaro Amano, Tokyo (JP); Taihei Michihata, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 46 days.

(21) Appl. No.: 15/897,185

(22) Filed: Feb. 15, 2018

(65) Prior Publication Data

US 2018/0262696 A1  Sep. 13, 2018

(30) Foreign Application Priority Data

Mar. 7, 2017 (JP) .................................. 2017-043239

(51) Int. Cl.
| | |
|---|---|
| *A61B 1/00* | (2006.01) |
| *A61B 1/04* | (2006.01) |
| *A61B 1/07* | (2006.01) |
| *H04N 5/345* | (2011.01) |
| *H04N 5/262* | (2006.01) |
| *H04N 5/232* | (2006.01) |
| *H04N 5/272* | (2006.01) |

(Continued)

(52) U.S. Cl.
CPC ......... *H04N 5/2628* (2013.01); *A61B 1/0005* (2013.01); *A61B 1/00006* (2013.01); *A61B 1/00009* (2013.01); *A61B 1/00105* (2013.01); *A61B 1/00195* (2013.01); *A61B 1/042* (2013.01); *A61B 1/07* (2013.01); *G02B 23/2446* (2013.01); *G02B 23/2484* (2013.01); *H04N 5/23203* (2013.01); *H04N 5/23293* (2013.01); *H04N 5/272* (2013.01); *H04N 5/3454* (2013.01); *G02B 23/2469* (2013.01); *H04N 2005/2255* (2013.01)

(58) Field of Classification Search
CPC .... A61B 1/00; G02B 23/2484; G02B 23/243; G02B 23/2415

See application file for complete search history.

(56) References Cited

U.S. PATENT DOCUMENTS

2002/0183590 A1* 12/2002 Ogawa ............... A61B 1/00041
 600/117
2007/0041655 A1*  2/2007 Ozawa ................... A61B 1/042
 382/266

(Continued)

FOREIGN PATENT DOCUMENTS

JP  2015-134039  7/2015

*Primary Examiner* — Clifford Hilaire

(74) *Attorney, Agent, or Firm* — Xsensus LLP

(57) ABSTRACT

An endoscope apparatus includes: an imaging apparatus that includes an imaging element configured to capture a subject image of inside of a subject, the imaging apparatus outputting an image signal obtained by capturing the subject image by the imaging element; a control apparatus configured to process the image signal to generate a video signal for display; and a signal transmission path configured to transmit the image signal from the imaging apparatus to the control apparatus. The imaging apparatus outputs, as the image signal, pixel signals of respective pixels in a specified pixel area out of a whole pixel area of the imaging element, the specified pixel area being smaller than the whole pixel area and containing the entire subject image.

4 Claims, 13 Drawing Sheets

(51) Int. Cl.
G02B 23/24 (2006.01)
H04N 5/225 (2006.01)

(56) References Cited

U.S. PATENT DOCUMENTS

| | | | | |
|---|---|---|---|---|
| 2014/0375781 A1* | 12/2014 | Ono | ............... | G02B 23/2484 |
| | | | | 348/61 |
| 2015/0145953 A1* | 5/2015 | Fujie | ............... | G02B 23/2415 |
| | | | | 348/45 |
| 2015/0243027 A1* | 8/2015 | Ichiki | ............... | G06K 9/4604 |
| | | | | 382/128 |
| 2018/0115685 A1* | 4/2018 | Hadley | ............ | A61B 1/00009 |

* cited by examiner

FIG.7
(a)
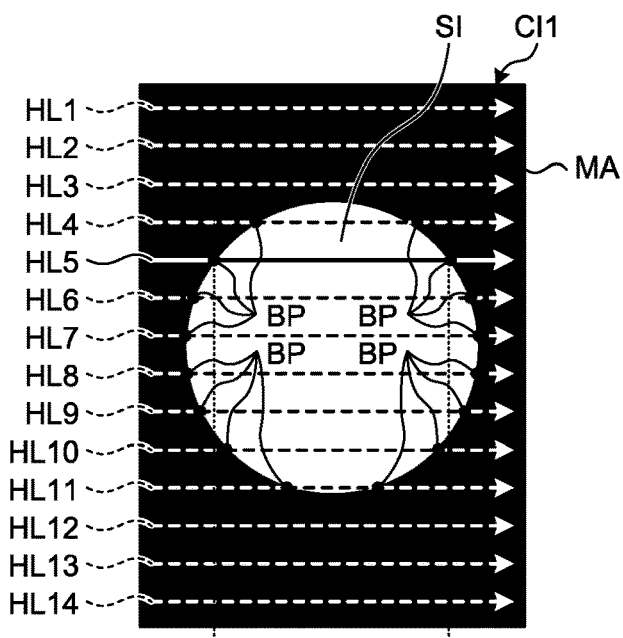
(b)
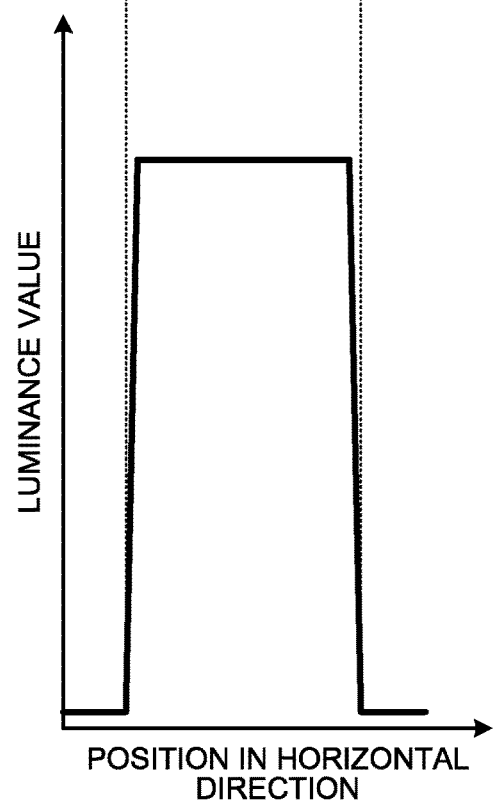

ENDOSCOPE APPARATUS

CROSS-REFERENCE TO RELATED APPLICATION

The present application claims priority to and incorporates by reference the entire contents of Japanese Patent Application No. 2017-043239 filed in Japan on Mar. 7, 2017.

BACKGROUND

The present disclosure relates to an endoscope apparatus for observing the inside of subjects such as humans and mechanical structures.

In the medical field or the industrial field, an endoscope apparatus for observing the inside of subjects such as humans and mechanical structures (refer to Japanese Laid-open Patent Publication No. 2015-134039, for example) has been known.

The endoscope apparatus described in Japanese Laid-open Patent Publication No. 2015-134039 includes an insertion unit that is inserted into the inside of a subject and captures a subject image of the inside of the subject from the tip, an imaging apparatus (a camera head) that has an imaging element capturing the subject image and outputs an image signal obtained by capturing the subject image by the imaging element, a control apparatus that processes the image signal to generate a video signal for display, and a signal transmission path (a composite cable) that transmits the image signal from the imaging apparatus to the control apparatus.

SUMMARY

In recent years, owing to higher resolution of imaging elements, image signals obtained by the capturing by the imaging elements have increased in the amount of information accordingly. In general, pixel signals from respective pixels in the whole pixel area of an imaging element are output as an image signal from an imaging apparatus to a control apparatus, thus increasing the amount of information and increasing a signal transmission path in size owing to an increased number of transmission paths, for example.

Given these circumstances, there is a need for a technique that may reduce the amount of information of the image signal and reduce the signal transmission path in size.

There is a need for an endoscope apparatus with a reduced amount of information of an image signal and with a reduced size of a signal transmission path.

An endoscope apparatus according to one aspect of the present disclosure may include: an imaging apparatus that includes an imaging element configured to capture a subject image of inside of a subject, the imaging apparatus outputting an image signal obtained by capturing the subject image by the imaging element; a control apparatus configured to process the image signal to generate a video signal for display; and a signal transmission path configured to transmit the image signal from the imaging apparatus to the control apparatus, wherein the imaging apparatus outputs, as the image signal, pixel signals of respective pixels in a specified pixel area out of a whole pixel area of the imaging element, the specified pixel area being smaller than the whole pixel area and containing the entire subject image.

BRIEF DESCRIPTION OF THE DRAWINGS

FIG. 7 is a diagram illustrating mask edge detection processing;

DETAILED DESCRIPTION

Figure 1:
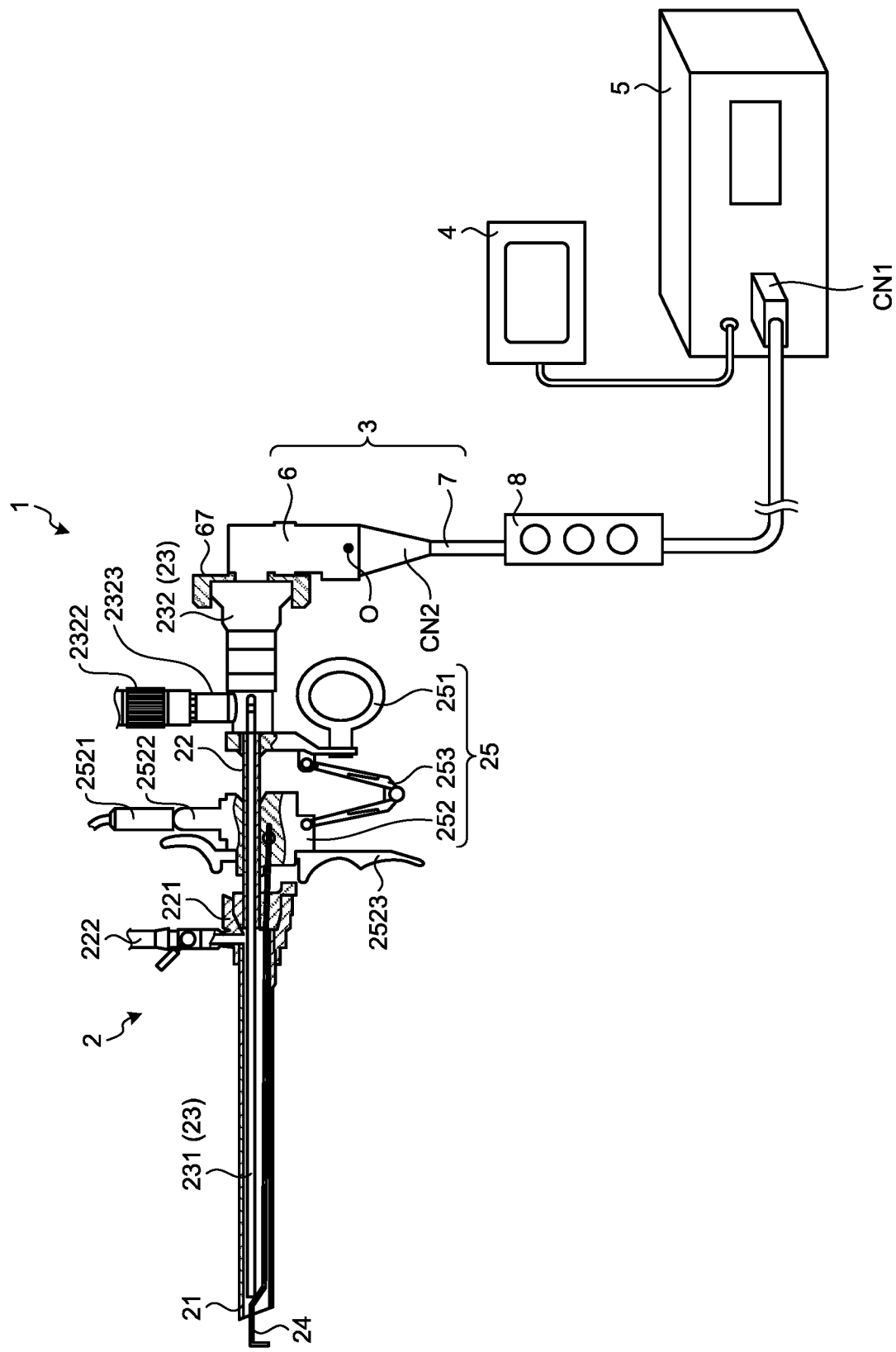
FIG. 1 is a diagram of a schematic configuration of an endoscope apparatus according a first embodiment.

The following describes modes for performing the present disclosure (hereinafter, embodiments) with reference to the accompanying drawings. The embodiments described below do not limit the present disclosure. In the drawings, the same parts are denoted by the same symbols.

First Embodiment

Schematic Configuration of Endoscope System

FIG. 1 is a diagram of a configuration of an endoscope apparatus 1 according to a first embodiment.

The endoscope apparatus 1 is an apparatus that is used in the medical field for treating (making an incision in, for example) living body tissue while the inside of a living body is being observed. As illustrated in FIG. 1, this endoscope apparatus 1 includes a resectoscope 2, an imaging apparatus 3 for endoscope use, a display apparatus 4, and a control apparatus 5.

The resectoscope 2 is a part that is inserted into the living body, captures a subject image, and treats the living body tissue. As illustrated in FIG. 1, this resectoscope 2 includes a sheath 21, a guide pipe 22, an endoscope 23, a resection electrode 24, and a handle 25.

The "distal end" described below means an end on a side to be inserted into the living body (the left end in FIG. 1). The "basal end" described below means an end on a side separated from the "distal end" (the right end in FIG. 1).

The sheath 21 is a part that has a cylindrical shape and is inserted into the living body.

The guide pipe 22 has an outer diameter dimension smaller than the inner diameter dimension of the sheath 21 and is inserted into the sheath 21 from the basal end side of the sheath 21. The distal end side of the guide pipe 22 is fixed to the basal end side of the sheath 21 via a mounting member 221 (FIG. 1).

The mounting member 221 is provided with a feeding port 222 for injecting liquid into the sheath 21 and feeding the liquid from the distal end of the sheath 21.

The endoscope 23 is a part that captures the subject image and includes an insertion unit 231 and an eyepiece unit 232 as illustrated in FIG. 1.

The insertion unit 231 is fixed to the inside of the guide pipe 22 and is inserted into the sheath 21. Provided within this insertion unit 231 is an optical system that includes one or a plurality of lenses and collects the subject image.

The eyepiece unit 232 is coupled to the basal end of the insertion unit 231. Provided within this eyepiece unit 232 is an eyepiece optical system 2321 (refer to FIG. 3) that emits the subject image collected by the optical system within the insertion unit 231 to the outside from the basal end of the eyepiece unit 232. The eyepiece unit 232 is formed in a tapered shape having a more enlarged diameter toward the basal end, and the imaging apparatus 3 for endoscope use is detachably connected to the enlarged diameter part.

The eyepiece unit 232 is provided with a light source connector 2323 to which a light guide 2322 is connected. Thus, light supplied from a light source apparatus (not illustrated) to the light guide 2322 is supplied to the insertion unit 231 via the eyepiece unit 232. The light supplied to the insertion unit 231 is emitted from the distal end of the insertion unit 231 to be applied to the inside of the living body. The light (the subject image) applied to the inside of the living body and reflected by the inside of the living body is emitted from the basal end of the eyepiece unit 232 via the optical system within the insertion unit 231 and the eyepiece optical system 2321.

The resection electrode 24 is inserted into the sheath 21 via the mounting member 221, and the distal end thereof protrudes from the distal end of the sheath 21. The resection electrode 24, bringing its distal end part into contact with the living body tissue, treats the living body tissue through a high-frequency current.

The handle 25 is a part through which a doctor or the like grips the resectoscope 2 and operates the resection electrode 24. As illustrated in FIG. 1, this handle 25 includes a fixed ring 251, a slider 252, and a spring 253.

The fixed ring 251 is a part on which the doctor or the like hooks the thumb and is fixed to the basal end side of the guide pipe 22.

The slider 252, into which the guide pipe 22 is inserted, is movable in the right-and-left direction in FIG. 1 along the guide pipe 22.

As illustrated in FIG. 1, the basal end of the resection electrode 24 is fixed to this slider 252. Thus, the resection electrode 24 advances and retracts in the right-and-left direction in FIG. 1 within the sheath 21 along with the movement of the slider 252.

The slider 252 is provided with a power supply connector 2522 to which a high-frequency power supply cord 2521 connected to a high-frequency power supply (not illustrated) is connected. This power supply connector 2522 is electrically connected to the basal end of the resection electrode 24 via a lead wire (no illustrated).

Furthermore, as illustrated in FIG. 1, the slider 252 is provided with a finger-hooking member 2523 on which the doctor or the like hooks fingers other than the thumb to move the slider 252 (advance and retract the resection electrode 24).

The spring 253 has a substantially U shape, in which one end thereof is mounted on the fixed ring 251 and the other end thereof is mounted on the slider 252. The spring 253 biases the slider 252 to a side separating from the fixed ring 251.

Thus, the doctor or the like hooks the fingers on the fixed ring 251 and the finger-hooking member 2523 and pulls the finger-hooking member 2523 against the biasing force of the spring 253, thereby moving the slider 252 to the basal end side (moving the resection electrode 24 to the basal end side). When the doctor or the like moves the finger off the finger-hooking member 2523, the slider 252 (the resection electrode 24) moves to the distal end side through the biasing force of the spring 253.

The imaging apparatus 3 for endoscope use is detachably connected to the eyepiece unit 232 of the resectoscope 2 (the endoscope 23). The imaging apparatus 3 for endoscope use captures the subject image captured by the endoscope 23 (the subject image emitted from the eyepiece unit 232) and outputs an image signal (a RAW signal) by the capturing under the control of the control apparatus 5. The image signal is an image signal of 4 K or above, for example.

A detailed configuration of the imaging apparatus 3 for endoscope use will be described below.

The display apparatus 4 includes a display using liquid crystals, organic electro luminescence (EL), or the like and displays an image for observation based on a video signal from the control apparatus 5 under the control of the control apparatus 5.

The control apparatus 5 includes a central processing unit (CPU) and comprehensively controls the operation of the imaging apparatus 3 for endoscope use, the display apparatus 4, and the light source apparatus (not illustrated).

A detailed configuration of the control apparatus 5 will be described below.

Configuration of Imaging Apparatus for Endoscope Use

The following describes the configuration of the imaging apparatus 3 for endoscope use.

Figure 2:
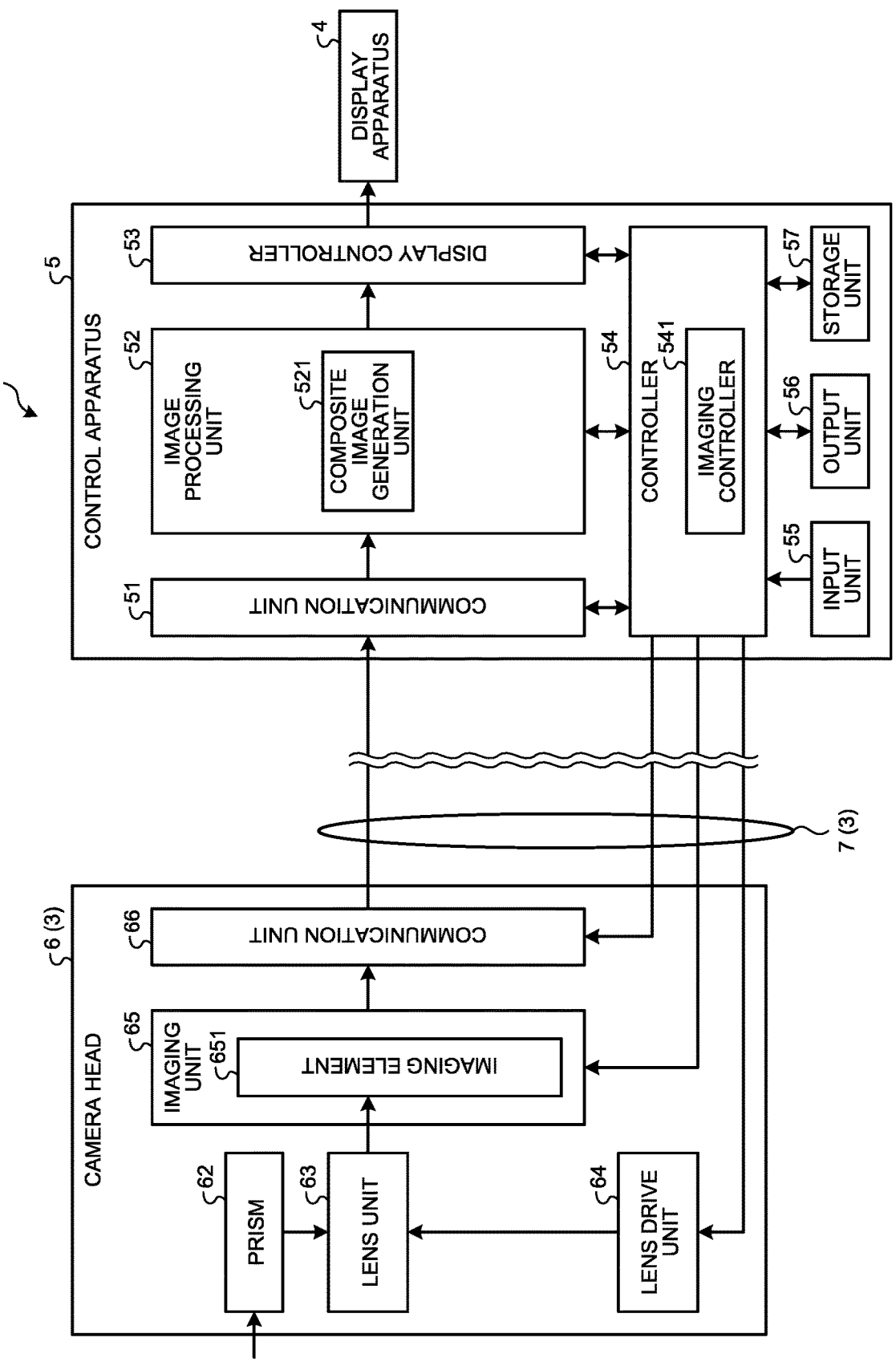
FIG. 2 is a block diagram of a configuration of an imaging apparatus for endoscope use and a control apparatus.

FIG. 2 is a block diagram of the configuration of the imaging apparatus 3 for endoscope use and the control apparatus 5. FIG. 2 omits the illustration of an operating unit 8 and connectors CN1 and CN2 for the convenience of description.

As illustrated in FIG. 1 or FIG. 2, the imaging apparatus 3 for endoscope use includes a camera head 6 and a cable 7.

Figure 3:
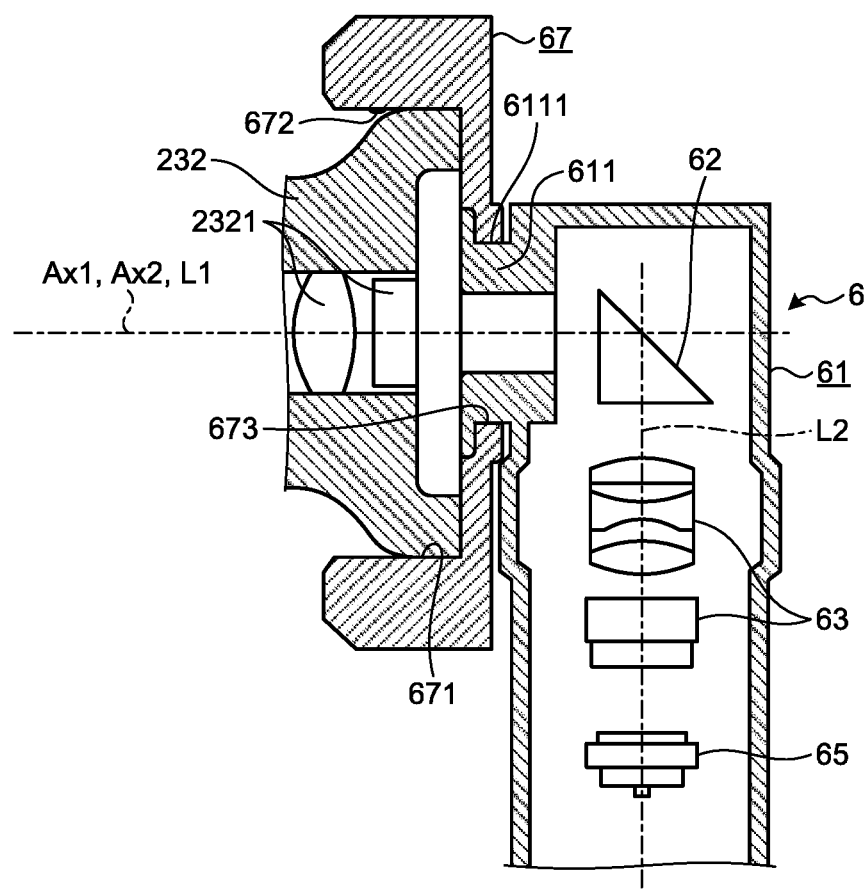
FIG. 3 is a sectional view of a connecting part between an eyepiece unit and a camera head.

FIG. 3 is a sectional view of a connecting part between the eyepiece unit 232 and the camera head 6. FIG. 3 omits the illustration of a drive unit 64 and a communication unit 66 for the convenience of description.

As illustrated in FIG. 1 or FIG. 3, the camera head 6 is a part detachably connected to the eyepiece unit 232 of the endoscope 23 and has a function of an imaging apparatus according to the present disclosure. As illustrated in FIG. 2 or FIG. 3, this camera head 6 includes a camera head housing 61 (FIG. 3), a prism 62, a lens unit 63, the drive unit 64 (FIG. 2), an imaging unit 65, and a communication unit 66 (FIG. 2) housed in the camera head housing 61.

The camera head housing 61 is a housing that houses therein the members 62 to 66. As illustrated in FIG. 3, this camera head housing 61 is provided with a protruding part 611 having a cylindrical shape that causes the inside and the outside of the camera head housing 61 to communicate with each other. Formed on the outer peripheral face of this protruding part 611 is an annular groove 6111 extending in a rotation direction about a central axis Ax1 of the protruding part 611. A mounting member 67 is mounted on the annular groove 6111.

The mounting member 67 is a member for mounting the camera head 6 on the eyepiece unit 232 and has a cylindrical shape.

In this mounting member 67, provided on an end face on one end side is a fitting hole 671 that is recessed toward the other end and into which the eyepiece unit 232 is fit. Provided to the inner peripheral face of the fitting hole 671 is a locking protrusion 672 that is locked to the outer peripheral face of the eyepiece unit 232. With the eyepiece unit 232 fit into the fitting hole 671, an optical axis L1 of the endoscope 23 coincides with a central axis Ax2 of the mounting member 67.

In the mounting member 67, provided on an end face on the other end side is a communication hole 673 that communicates with the fitting hole 671. The edge of the communication hole 673 fits into the annular groove 6111, whereby the mounting member 67 is mounted on the protruding part 611. In this state, the central axis Ax2 of the mounting member 67 and the central axis Ax1 of the protruding part 611 coincide with each other. The mounting member 67 is rotatable about the central axis Ax1 (Ax2).

Consequently, the camera head 6 is rotatable about the optical axis L1 relative to the eyepiece unit 232 of the endoscope 23 via the mounting member 67. The camera head 6 is configured to cause its center of gravity O (FIG. 1) to be located at a position (a position below the optical axis L1 in FIG. 3) deviated from the optical axis L1 (a rotational central axis with respect to the eyepiece unit 232). The camera head 6 is configured to rotate about the optical axis L1 regardless of the rotation of the resectoscope 2 about the optical axis L1 to cause an optical axis L2 (FIG. 3) set within the camera head housing 61 to constantly have an attitude along the vertical direction (an attitude in which the center of gravity O is located below the optical axis L1).

As illustrated in FIG. 3, the prism 62 is arranged on the central axis Ax1 of the protruding part 611 (on the optical axis L1) to deflect the travel direction of the subject image captured by the endoscope 23. Specifically, the prism 62 deflects the travel direction of the subject image emitted from the eyepiece unit 232 and captured within the camera head housing 61 via the protruding part 611 (the subject image traveling along the optical axis L1) by substantially 90 degrees and causes the subject image to travel along the optical axis L2.

As illustrated in FIG. 3, the lens unit 63 is arranged on the optical axis L2. The lens unit 63 includes one or a plurality of lenses and forms the subject image via the prism 62 onto an imaging plane of the imaging unit 65 (an imaging element 651). The lens unit 63 is provided with an optical zooming function (not illustrated) that moves the one or a plurality of lenses to change the angle of view and a focusing function (not illustrated) that changes a focus.

The drive unit 64 operates the optical zooming function and the focusing function to change the angle of view and the focus of the lens unit 63 under the control of the control apparatus 5 or the operating unit 8 (FIG. 1).

As illustrated in FIG. 3, the imaging unit 65 is arranged on the optical axis L2. The imaging unit 65 captures the subject image focused by the lens unit 63 under the control of the control apparatus 5. This imaging unit 65 includes a sensor chip that integrally forms the imaging element 651 (FIG. 2) such as a complementary metal oxide semiconductor (CMOS) that receives the subject image focused by the lens unit 63 and converts it into an electric signal and a signal processing unit (not illustrated) that performs signal processing (A/D conversion and the like) on the electric signal (an analog signal) from the imaging element 651 to output an image signal, and outputs the image signal after the A/D conversion (a RAW signal (a digital signal)). The signal processing unit (not illustrated) may be separate from the imaging element 651 without being integrally formed therewith.

Figure 4:
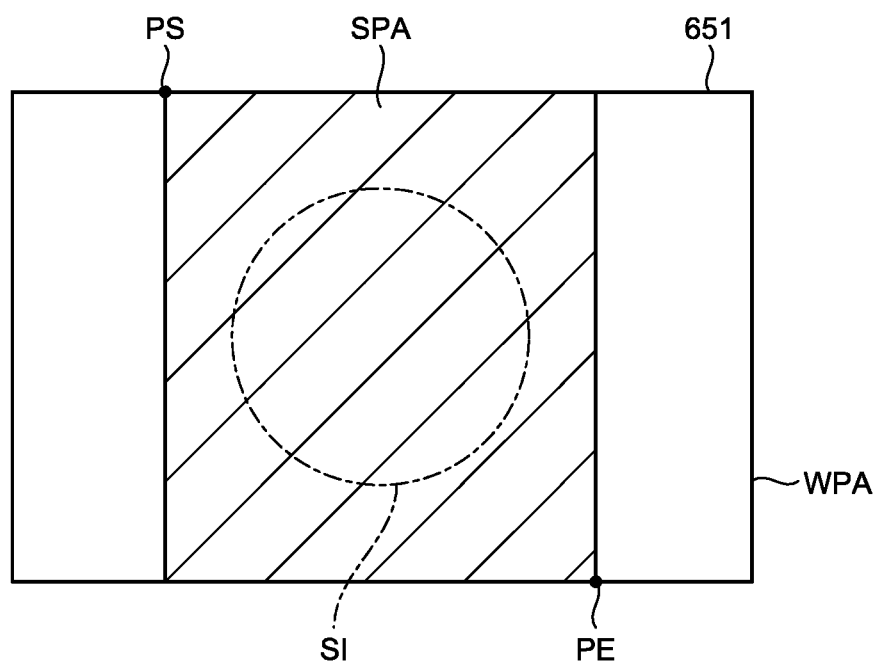
FIG. 4 is a diagram of a specified pixel area read from an imaging element.

FIG. 4 is a diagram of a specified pixel area SPA read from the imaging element 651.

In the imaging element 651, as illustrated in FIG. 4, pixel signals are read from only respective pixels in the specified pixel area SPA (the hatched area in FIG. 4) corresponding to a reading starting position PS and a reading ending position PE each set in advance under the control of the control apparatus 5.

In the first embodiment, the imaging apparatus 3 for endoscope use is an imaging apparatus for endoscope use exclusive for the resectoscope 2 for the urinary organs, for example. Light having a substantially circular section (a subject image SI (FIG. 4)) reflected by the inside of the living body and collected to the inside of the insertion unit 231 is focused with a fixed size at a fixed position in a whole pixel area WPA (the area shown by the largest rectangle in FIG. 4) of the imaging element 651. The specified pixel area SPA is set to be a rectangular area that is smaller than the whole pixel area WPA of the imaging element 651 and contains the entire subject image SI.

The imaging unit 65 outputs the pixel signals read from only the respective pixels in the specified pixel area SPA, not in the whole pixel area WPA, as the image signal (the RAW signal (the digital signal)).

The communication unit 66 functions as a transmitter that transmits the image signal (the RAW signal (the digital signal)) output from the imaging unit 65 to the control apparatus 5 via the cable 7. This communication unit 66 includes a high-speed serial interface that performs communication of the image signal at a transmission rate of 1 Gbps or more with the control apparatus 5, for example.

One end of the cable 7 is detachably connected to the control apparatus 5 via the connector CN1 (FIG. 1), whereas the other end thereof is detachably connected to the camera head 6 via the connector CN2 (FIG. 1). The cable 7 transmits the image signal output from the camera head 6 to the control apparatus 5 and transmits a control signal, a sync signal, a clock, electric power, and the like output from the control apparatus 5 to the camera head 6. Thus, the cable 7 has a function as a signal transmission path according to the present disclosure.

For the transmission of the image signal from the camera head 6 to the control apparatus 5 via the cable 7, the image signal, for example, may be transmitted via an optical signal or transmitted via an electric signal. The same holds true for the transmission of the control signal, the sync signal, and the clock from the control apparatus 5 to the camera head 6 via the cable 7.

As illustrated in FIG. 1, the cable 7 is provided with the operating unit 8 that receives various kinds of operations (instructions on image quality adjustment (such as white balance adjustment or brightness adjustment) on the image for observation and instructions for changing the angle of view and/or the focus of the lens unit 63, for example) from the doctor or the like.

Configuration of Control Apparatus

The following describes the configuration of the control apparatus 5 with reference to FIG. 2.

As illustrated in FIG. 2, the control apparatus 5 includes a communication unit 51, an image processing unit 52, a display controller 53, a controller 54, an input unit 55, an output unit 56, and a storage unit 57.

The communication unit 51 functions as a receiver that receives the image signal (the RAW signal (the digital signal)) output from the camera head 6 (the communication unit 66) via the cable 7. This communication unit 51 includes a high-speed serial interface that performs communication of the image signal at a transmission rate of 1 Gbps or more with the communication unit 66, for example.

The image processing unit 52 process the image signal (the RAW signal (the digital signal)) output from the camera head 6 (the communication unit 66) and received by the communication unit 51 under the control of the controller 54.

The image processing unit 52 performs RAW processing such as optical black subtraction processing or demosaicing processing on the image signal (the RAW signal (the digital signal)), for example, to convert the RAW signal (the image signal) into an RGB signal (an image signal). In addition, the image processing unit 52 performs RGB processing such as white balance adjustment processing, RGB gamma correction, or YC conversion (conversion of the RGB signal into a luminance signal and a color-difference signal (a Y, $C_B/C_R$ signal)) on the RGB signal (the image signal). Furthermore, the image processing unit 52 executes YC processing such as color-difference correction or noise reduction on the Y, $C_B/C_R$ signal (an image signal).

As illustrated in FIG. 2, the image processing unit 52 includes a composite image generation unit 521 configured to execute composite image generation processing shown below.

Figure 5:
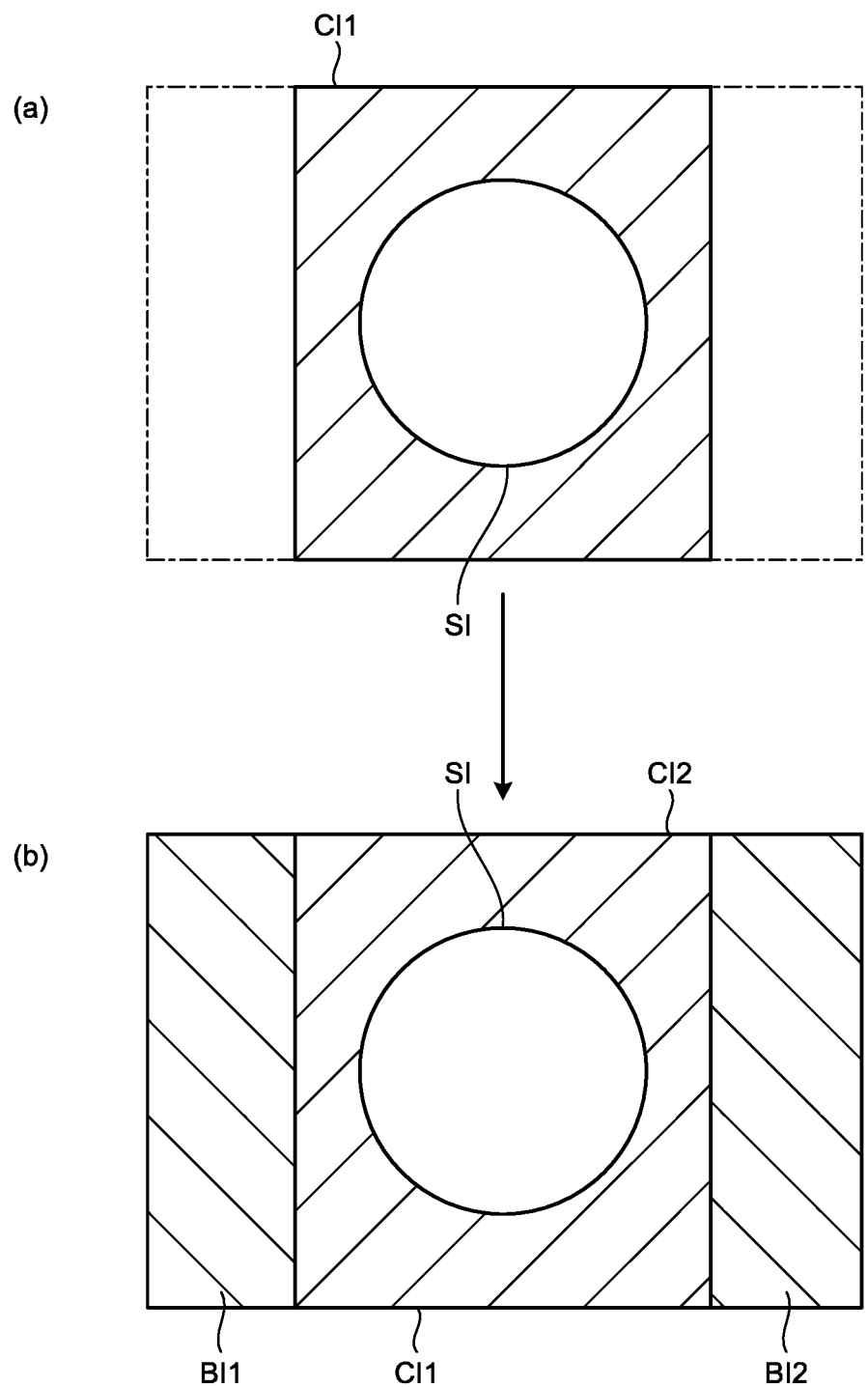
FIG. 5 is a diagram illustrating how a composite image is generated from a captured image based on an image signal output from the camera head.

FIG. 5 is a diagram illustrating how a composite image CI2 is generated from a captured image CI1 based on the image signal output from the camera head 6. Specifically, (a) of FIG. 5 is a diagram of the captured image CI1 based on the image signal output from the camera head 6. (b) of FIG. 5 is a diagram of the composite image CI2 generated by the composite image generation processing.

Specifically, as illustrated in FIG. 5, the composite image generation unit 521 executes the composite image generation processing that adds black-level images BI1 and BI2 to both sides of the captured image CI1 based on the image signal (the RAW signal, the RGB signal, or the Y, $C_B/C_R$ signal) to generate the composite image CI2 having the same aspect ratio as that of a display screen of the display apparatus 4. Thus, the composite image generation unit 521 has a function as a second composite image generation unit according to the present disclosure.

The display controller 53 generates a video signal for display based on the image signals (the Y, $C_B/C_R$ signal) processed by the image processing unit 52 under the control of the controller 54. The display controller 53 then causes the display apparatus 4 to display the composite image CI2 based on the video signal for display.

The controller 54 includes a CPU, for example, controls the operations of the camera head 6, the display apparatus 4, and the light source apparatus (not illustrated), and controls the operation of the entire control apparatus 5. As illustrated in FIG. 2, this controller 54 includes an imaging controller 541.

The imaging controller 541 reads the reading starting position PS and the reading ending position PE of the imaging element 651 from the storage unit 57 and gives instructions on the reading starting position PS and the reading ending position PE to the imaging unit 65 via the cable 7. In the imaging element 651, the pixel signals are read from only the respective pixels in the specified pixel area SPA corresponding to the reading starting position PS and the reading ending position PE.

The input unit 55 includes an operating device such as a mouse, a keyboard, and a touch panel, and receives user operations by a user such as a doctor. The input unit 55 outputs operation signals responsive to the user operations to the controller 54.

The output unit 56 includes a speaker or a printer and outputs various kinds of information.

The storage unit 57 stores therein computer programs executed by the controller 54, information used for the processing by the controller 54, and the like.

The first embodiment described above produces the following effect.

In the endoscope apparatus 1 according to the first embodiment, the camera head 6 outputs the pixel signals of the respective pixels in the specified pixel area SPA, out of the whole pixel area WPA of the imaging element 651, as the image signal (the RAW signal) to the control apparatus 5 via the cable 7. The specified pixel area SPA is smaller than the whole pixel area WPA and contains the entire subject image SI. Compared with outputting the pixel signals from the respective pixels in the whole pixel area WPA of the imaging element 651 as the image signal from the camera head 6 to the control apparatus 5, the amount of information of the image signal (the RAW signal) output from the camera head 6 to the control apparatus 5 may be reduced while the information on the subject image SI used for observation is contained.

Consequently, the endoscope apparatus 1 according to the first embodiment produces an effect of making it possible to reduce the amount of information of the image signal (the RAW signal) and reduce the cable 7 in size owing to a reduced number of transmission paths, for example.

The lens unit 63 is only used to focus the subject image SI onto the specified pixel area SPA, which is a relatively small area. Consequently, there is no need to use a large lens unit for the lens unit 63, and the lens unit 63 may be reduced in size. Thus, the camera head 6 may be reduced in size and weight, and living body tissue may be easily treated while the resectoscope 2 to be inserted into a living body is held by an operator with his/her hands.

In the endoscope apparatus 1 according to the first embodiment, in the imaging element 651, the pixel signals are read from only the respective pixels in the specified pixel area SPA.

Consequently, compared with reading the pixel signals from the respective pixels in the whole pixel area WPA, the power consumption of the imaging element 651 may be reduced. In addition, the amount of information of the image signal (the RAW signal) output from the camera head 6 to the control apparatus 5 may be reduced, whereby the load on the communication unit 66 may be reduced, and the power consumption of the communication unit 66 may also be reduced. Thus, the power consumption of the entire camera head 6 may be reduced.

Along with the reduction in the power consumption of the entire camera head 6, a temperature increase of the camera head 6 caused by the heating of the imaging element 651 and the communication unit 66 may be reduced.

Second Embodiment

The following describes a second embodiment.

In the following, components similar to those of the first embodiment are denoted by the same symbols, and detailed descriptions thereof are omitted or simplified.

Figure 6:
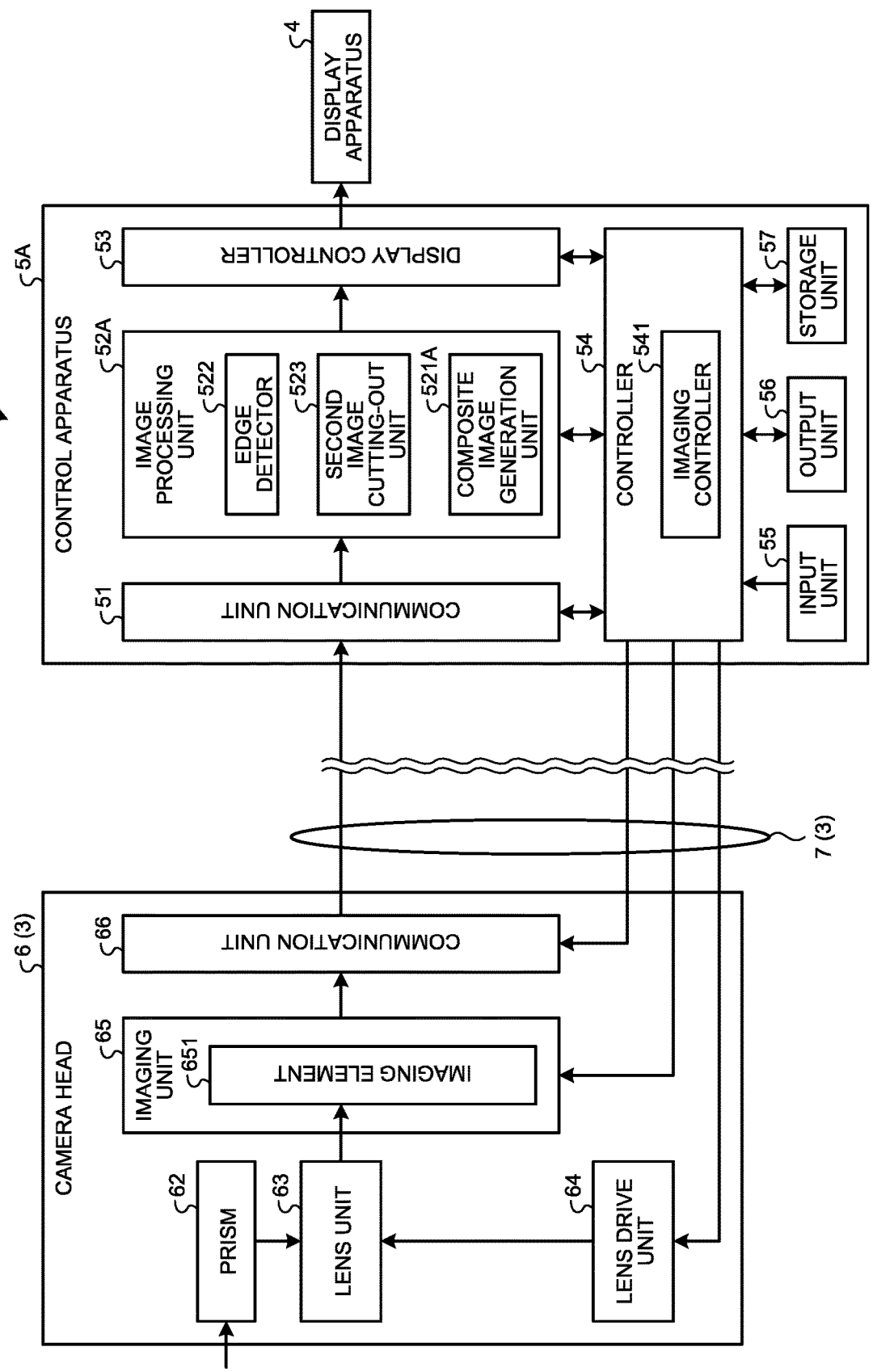
FIG. 6 is a diagram of a schematic configuration of an endoscope apparatus according a second embodiment.

FIG. 6 is a diagram corresponding to FIG. 2 and is a diagram of a schematic configuration of an endoscope apparatus 1A according to the second embodiment.

In the endoscope apparatus 1A (a control apparatus 5A) according to the second embodiment, as illustrated in FIG. 6, an image processing unit 52A that generates a composite image in a different way from the image processing unit 52 is used in place of the image processing unit 52 for the endoscope apparatus 1 described in the first embodiment.

As illustrated in FIG. 6, the image processing unit 52A includes an edge detector 522, a second image cutting-out unit 523, and a composite image generation unit 521A.

The edge detector 522 executes mask edge detection processing shown below.

FIG. 7 is a diagram illustrating the mask edge detection processing. Specifically, (a) of FIG. 7 is a diagram of the captured image CI1 based on the image signal output from the camera head 6. (b) of FIG. 7 is a diagram of the distribution of a luminance value on a horizontal line HL5 in the captured image CI1 illustrated in (a) of FIG. 7.

The edge detector 522 executes the mask edge detection processing, thereby detecting boundary points BP ((a) of FIG. 7) between the subject image SI and a masked area MA (the black-filled area in (a) of FIG. 7) other than the subject image SI.

Specifically, as illustrated in (a) of FIG. 7, the edge detector 522 acquires the luminance signal (the Y signal) in the image signal (the Y, $C_B/C_R$ signal) processed by the image processing unit 52. Based on the luminance signal (the Y signal), the edge detector 522 detects respective pieces of distribution of the luminance value on a plurality of (14 in the second embodiment) horizontal lines HL1 to HL14 within the captured image CI1. In the captured image CI1, the area of the subject image SI is higher than the masked area MA in the luminance value. Thus, the luminance distribution on the horizontal line HL5 is higher in the luminance value in a part between the two boundary points BP between the subject image SI and the masked area MA, and is lower in the luminance value in the other part, as illustrated in (b) of FIG. 7, for example. Consequently, the edge detector 522 detects the respective pieces of distribution of the luminance value on the horizontal lines HL1 to HL14 and may thereby detect a plurality of boundary points BP between the subject image SI and the masked area MA.

Figure 8:
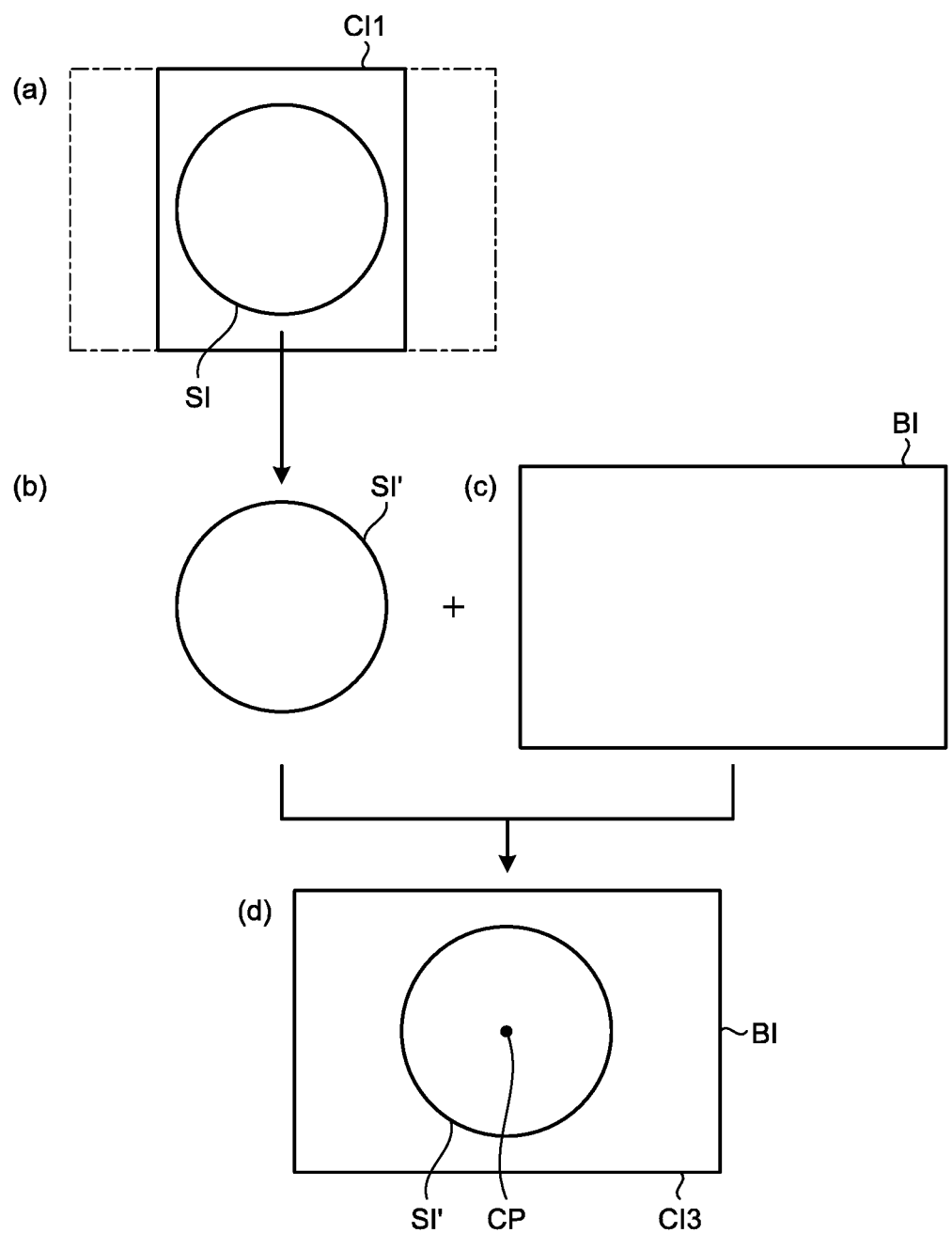
FIG. 8 is a diagram illustrating how a composite image is generated from a captured image based on an image signal output from the camera head.

FIG. 8 is a diagram illustrating how a composite image CI3 is generated from the captured image CI1 based on the image signal output from the camera head 6. Specifically, (a) of FIG. 8 is a diagram of the captured image CI1 based on the image signal output from the camera head 6. (b) of FIG. 8 is a diagram of an image SI' of the subject image generated by image cutting-out processing by the second image cutting-out unit 523. (c) of FIG. 8 is a diagram of a background image BI used in the composite image generation processing by the composite image generation unit 521A. (d) of FIG. 8 is a diagram of the composite image CI3 generated by the composite image generation processing.

As illustrated in (a) of FIG. 8 and (b) of FIG. 8, the second image cutting-out unit 523 executes the image cutting-out processing that cuts the image SI' of the subject image corresponding to the subject image SI surrounded by the boundary points BP detected by the edge detector 522 out of the captured image CI1 based on the image signal (the RAW signal, the RGB signal, or the Y, $C_B/C_R$ signal).

As illustrated in (b) of FIG. 8 to (d) of FIG. 8, the composite image generation unit 521A executes the composite image generation processing that generates the composite image CI3 in which the image SI' of the subject image cut out by the second image cutting-out unit 523 is superimposed onto the background image BI with a black level, for example, having the same aspect ratio as that of the display screen of the display apparatus 4. In this process, the composite image generation unit 521A superimposes the image SI' of the subject image onto the background image BI so as to cause respective central positions CP to coincide with each other. Thus, the composite image generation unit 521A has a function as a first composite image generation unit according to the present disclosure.

The display controller 53 causes the display apparatus 4 to display the composite image CI3 generated by the composite image generation unit 521A.

The background image BI may be an image having other colors and/or patterns, not limited to the black-level image.

The second embodiment described above produces the following effect in addition to an effect similar to that of the first embodiment.

When the black-level images BI1 and BI2 are added to both sides of the captured image CI1 to generate the composite image CI2 as in the composite image generation processing described in the first embodiment, the following problem may occur.

When the black level of the masked area MA and the black level of the images BI1 and BI2 are different from each other, the boundary between the captured image CI1 and the images BI1 and BI2 is conspicuous in the composite image CI2, and the display quality of the image for observation (the composite image CI2) is impaired.

The endoscope apparatus 1A according to the second embodiment executes the composite image generation processing that generates the composite image CI3 in which the image SI' of the subject image is superimposed onto the background image BI. Consequently, the above-described boundary is not present, and the display quality of the image for observation (the composite image CI3) is not impaired.

In the composite image generation processing, the image SI' of the subject image is superimposed onto the background mage BI so as to cause the respective central positions CP to coincide with each other. Consequently, when scaling processing or the like is performed on the composite image CI3, the scaling processing is performed with the central position CP centered. Thus, the display quality is not impaired similarly as the above.

Third Embodiment

The following describes a third embodiment.

In the following, components similar to those of the second embodiment are denoted by the same symbols, and detailed descriptions thereof are omitted or simplified.

Figure 9:
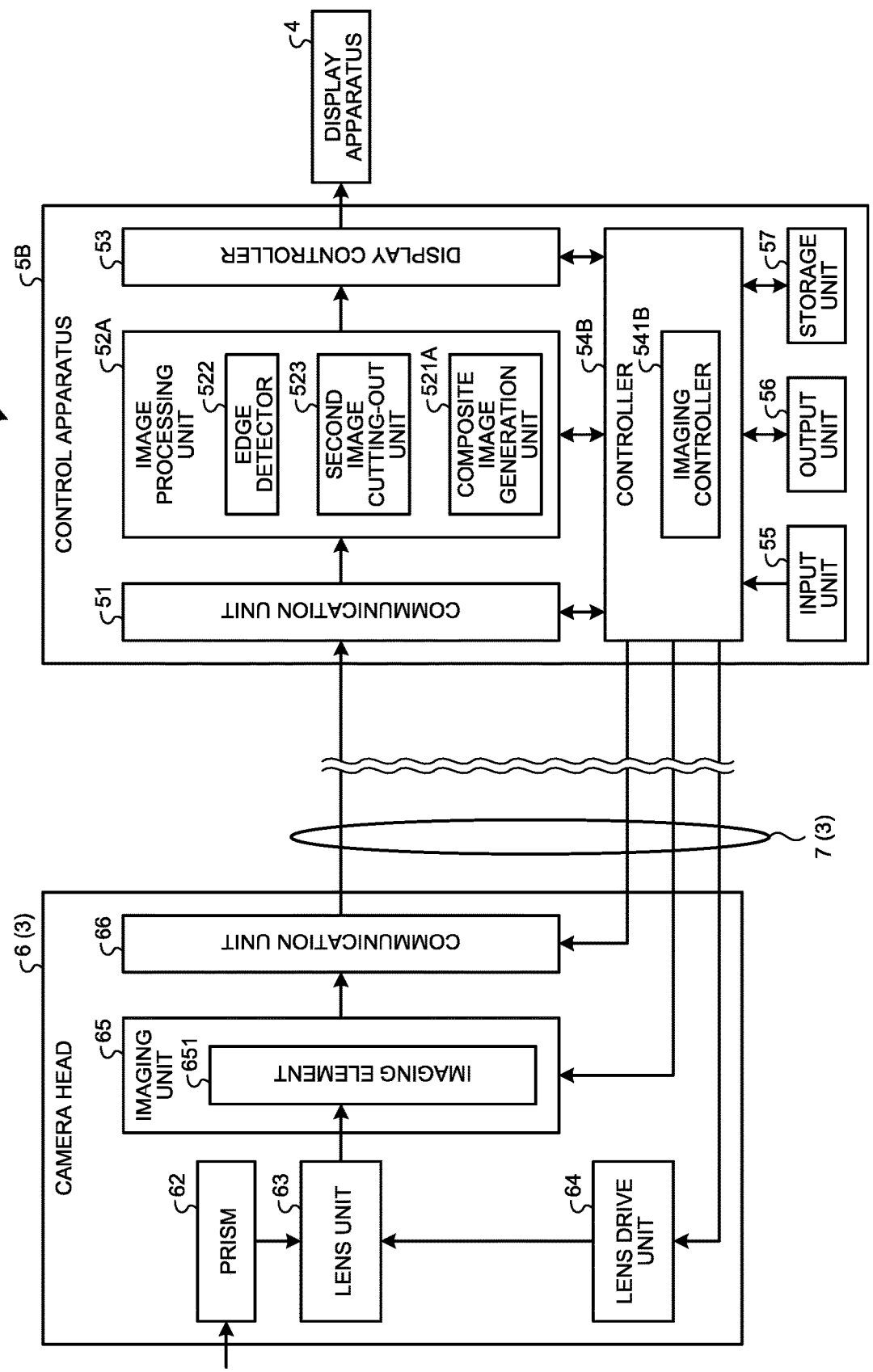
FIG. 9 is a diagram of a schematic configuration of an endoscope apparatus according a third embodiment.

FIG. 9 is a diagram corresponding to FIG. 6 and is a diagram of a schematic configuration of an endoscope apparatus 1B according to the third embodiment.

In the endoscope apparatus 1B (a control apparatus 5B) according to the third embodiment, as illustrated in FIG. 9, a controller 54B (an imaging controller 541B) to which a new function is added to the controller 54 is used in place of the controller 54 for the endoscope apparatus 1A described in the second embodiment.

Figure 10A:
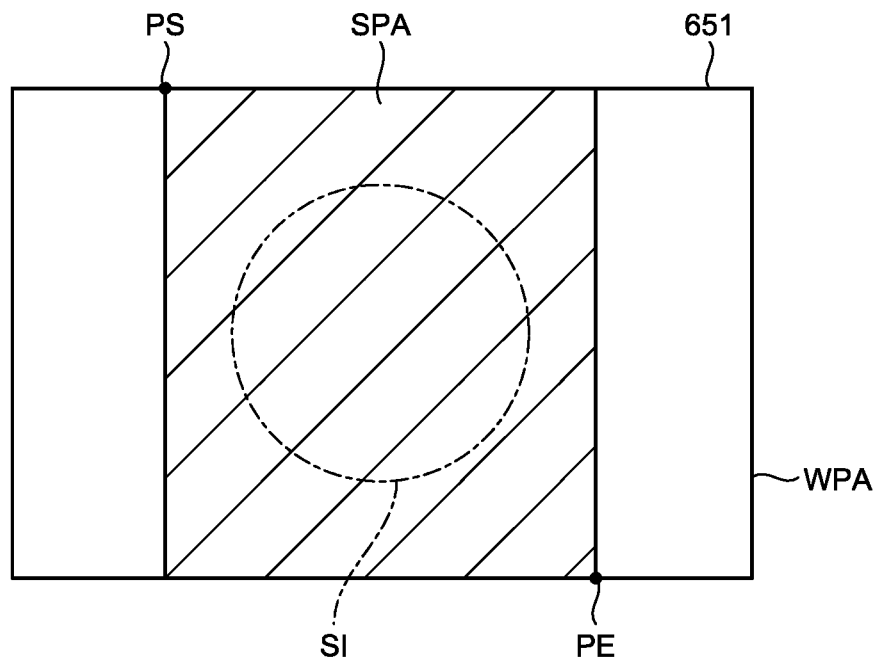
FIG. 10A is a diagram of the specified pixel area read from the imaging element.
Figure 10B:
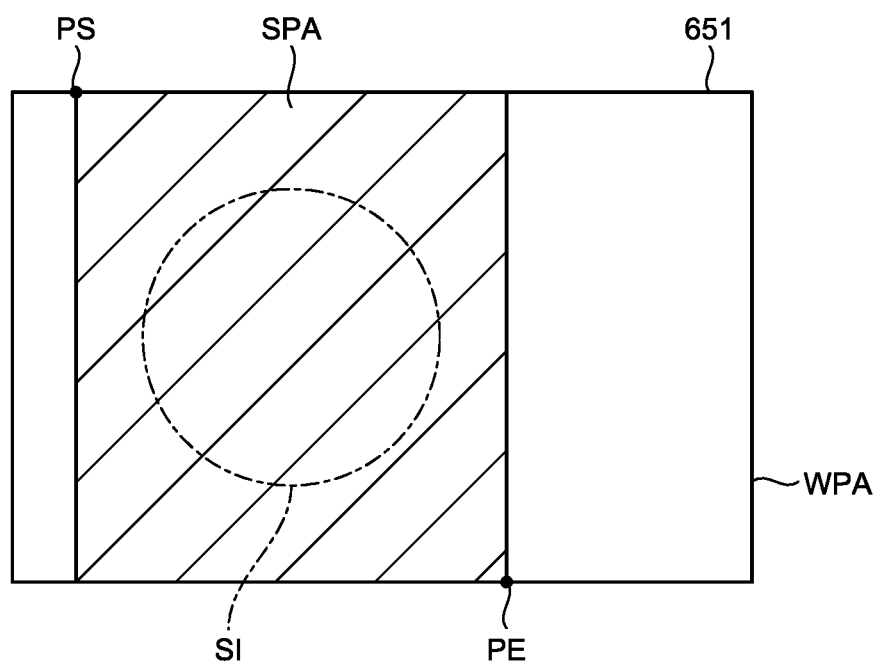
FIG. 10B is a diagram of the specified pixel area read from the imaging element.

FIG. 10A and FIG. 10B are diagrams of the specified pixel area SPA read from the imaging element 651.

The imaging controller 541B changes the reading starting position PS and the reading ending position PE to be instructed to the imaging unit 65 via the cable 7 as illustrated in FIG. 10A or FIG. 10B based on a processing result of the mask edge detection processing by the edge detector 522.

Specifically, when the position of the subject image SI surrounded by the boundary points BP deviates in the right-and-left direction within the captured image CI1 (when the central position of the subject image SI deviates in the right-and-left direction from the central position of the captured image CI1), the imaging controller 541B changes the reading starting position PS and the reading ending position PE in accordance with the deviation.

Even when the reading starting position PS and the reading ending position PE have been changed, the specified pixel area SPA corresponding to the reading starting position PS and the reading ending position PE is a rectangular area that is smaller than the whole pixel area WPA of the imaging element 651 and contains the entire subject image SI as illustrated in FIG. 10A or FIG. 10B.

In the imaging element 651, the pixel signals are read from only the respective pixels in the specified pixel area SPA corresponding to the reading starting position PS and the reading ending position PE indicated by the imaging controller 541B.

The third embodiment described above produces the following effect in addition to an effect similar to that of the second embodiment.

The endoscope apparatus 1B according to the third embodiment changes the specified pixel area SPA (the reading starting position PS and the reading ending position PE) in accordance with the position of the subject image SI surrounded by the boundary points BP within the captured image CI1.

Consequently, even when the optical axis L1 of the endoscope 23 has deviated from the central axes Ax1 and Ax2 of the protruding part 611 and the mounting member 67, respectively, for example, the specified pixel area SPA containing the entire subject image SI may be appropriately set.

Fourth Embodiment

The following describes a fourth embodiment.

In the following, components similar to those of the second embodiment are denoted by the same symbols, and detailed descriptions thereof are omitted or simplified.

Figure 11:
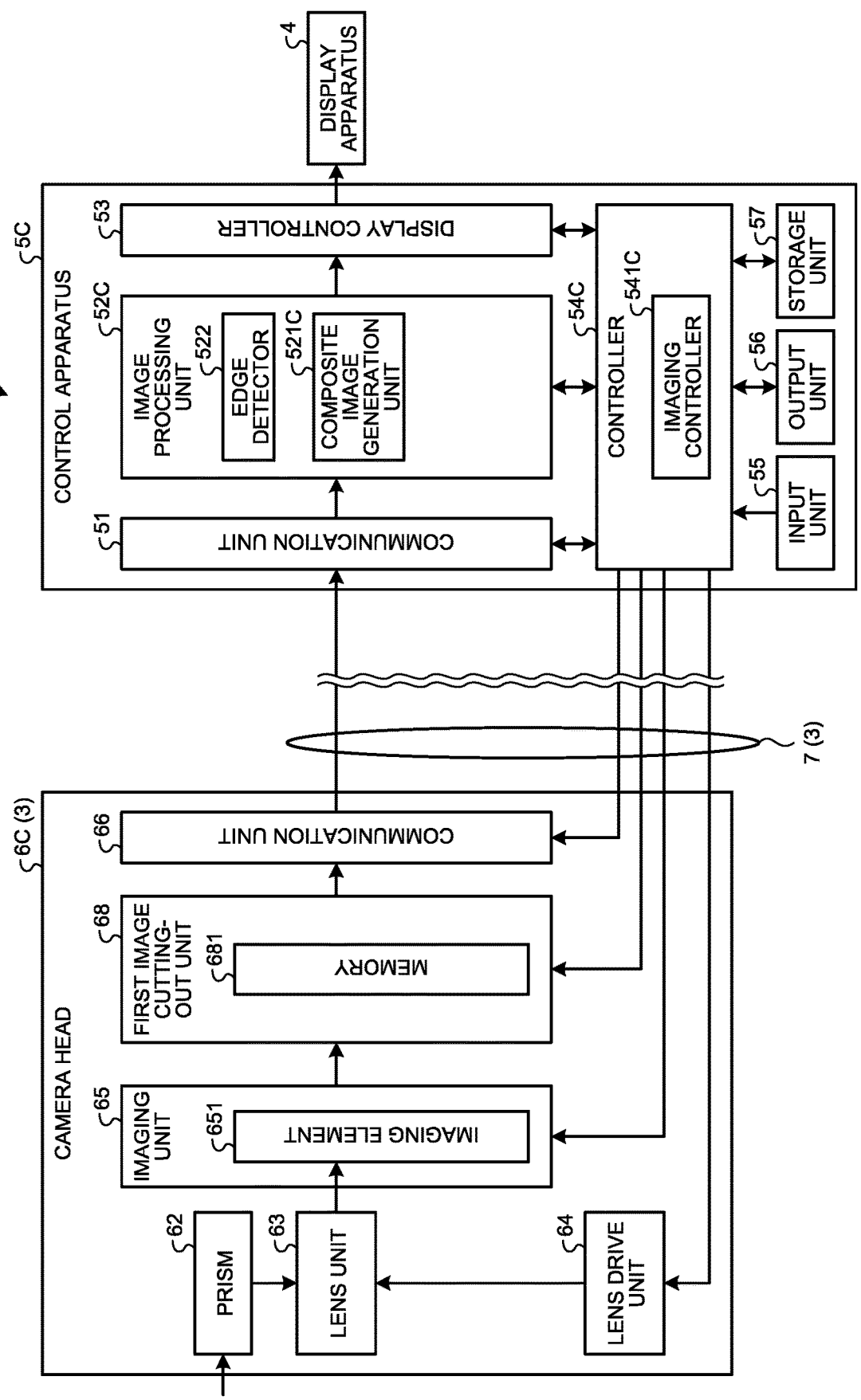
FIG. 11 is a diagram of a schematic configuration of an endoscope apparatus according to a fourth embodiment.

FIG. 11 is a diagram corresponding to FIG. 6 and is a diagram of a schematic configuration of an endoscope apparatus 1C according to the fourth embodiment.

The endoscope apparatus 1C according to the fourth embodiment is different from the endoscope apparatus 1A described in the second embodiment in the following point.

A camera head 6C included in the endoscope apparatus 1C adds a first image cutting-out unit 68 to the camera head 6 described in the second embodiment.

In addition, an image processing unit 52C included in the endoscope apparatus 1C (a control apparatus 5C) omits the second image cutting-out unit 523 from the image processing unit 52A described in the second embodiment and uses a composite image generation unit 521C configured to execute composite image generation processing substantially similar to that by the composite image generation unit 521A in place of the composite image generation unit 521A.

Furthermore, a controller 54C included in the endoscope apparatus 1C (the control apparatus 5C) uses an image controller 541C having a function different from that of the imaging controller 541 for the controller 54 described in the second embodiment.

Figure 12:
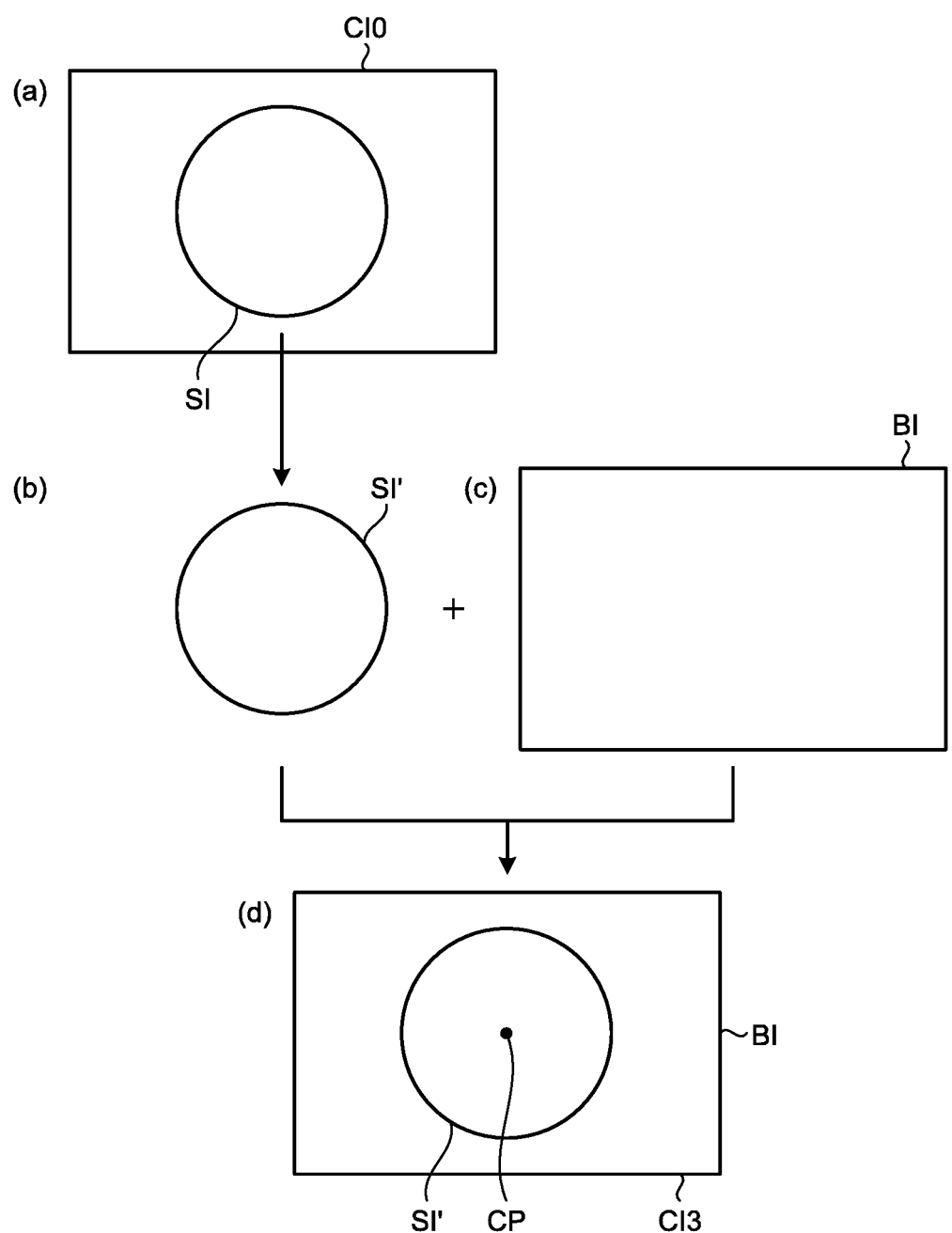
FIG. 12 is a diagram illustrating how the composite image is generated from a captured image captured by the imaging element.

FIG. 12 is a diagram illustrating how the composite image CI3 is generated from a captured image CI0 captured by the imaging element 651. Specifically, (a) of FIG. 12 is a diagram of the captured image CI0 captured by the imaging element 651. (b) of FIG. 12 is a diagram of the image SI' of the subject image generated by the image cutting-out processing by the first image cutting-out unit 68. (c) of FIG. 12 is a diagram of the background image BI used in the composite image generation processing by the composite image generation unit 521C. (d) of FIG. 12 is a diagram of the composite image CI3 generated by the composite image generation processing.

The image controller 541C gives instructions on the reading starting position PS and the reading ending position PE to the imaging unit 65 via the cable 7 so as to read the pixel signals from the respective pixels in the whole pixel area WPA of the imaging element 651. In the imaging element 651, the pixel signals are read from the respective pixels in the whole pixel area WPA corresponding to the reading starting position PS and the reading ending position PE. Thus, the captured image captured by the imaging element 651 is the captured image CI0 according to the whole pixel area WPA as illustrated in (a) of FIG. 12.

The image controller 541C sends notification of the processing result of the mask edge detection processing by the edge detector 522 (the pixel positions of the area of the subject image SI surrounded by the boundary points BP within the captured image CI0) to the first image cutting-out unit 68 via the cable 7.

The first image cutting-out unit 68 has a memory 681 and once stores the captured image CI0 captured by the imaging element 651 in the memory 681. The first image cutting-out unit 68 then executes the image cutting-out processing that reads only the image SI' of the subject image corresponding to the subject image SI surrounded by the boundary points BP from the captured image CI0 stored in the memory 681 in accordance with the notification from the image controller 541C as illustrated in (a) of FIG. 12 and (b) of FIG. 12.

The camera head 6C (the communication unit 66) then outputs the image signal (the RAW signal) corresponding to the image SI' of the subject image to the control apparatus 5C via the cable 7.

As illustrated in (b) of FIG. 12 to (d) of FIG. 12, the composite image generation unit 521C executes the composite image generation processing that generates the composite image CI3 in which the image SI' of the subject image based on the image signal (the RAW signal, the RGB signal, or the Y, $C_B/C_R$ signal) is superimposed onto the background image BI with a black level, for example, having the same aspect ratio as that of the display screen of the display apparatus 4. In this process, the composite image generation unit 521C superimposes the image SI' of the subject image onto the background image BI so as to cause the respective central positions CP to coincide with each other. Thus, the composite image generation unit 521C has a function as the first composite image generation unit according to the present disclosure.

The display controller 53 causes the display apparatus 4 to display the composite image CI3 generated by the composite image generation unit 521C.

The fourth embodiment described above produces the following effect in addition to an effect similar to that of the second embodiment.

In the endoscope apparatus 1C according to the fourth embodiment, the camera head 6C cuts the image SI' of the subject image out of the captured image CI0 corresponding to the whole pixel area WPA of the imaging element 651 and outputs the image signal (the RAW signal) corresponding to the image SI' of the subject image to the control apparatus 5C via the cable 7.

Consequently, the image signal (the RAW signal) output from the camera head 6C to the control apparatus 5C is only the information on the subject image SI used for observation, and the amount of information may be reduced most significantly. Consequently, the effect that the cable 7 may be reduced in size may be favorably achieved.

OTHER EMBODIMENTS

The modes for performing the present disclosure have been so far described; the present disclosure is not limited to only the first to the fourth embodiments.

Figure 13:
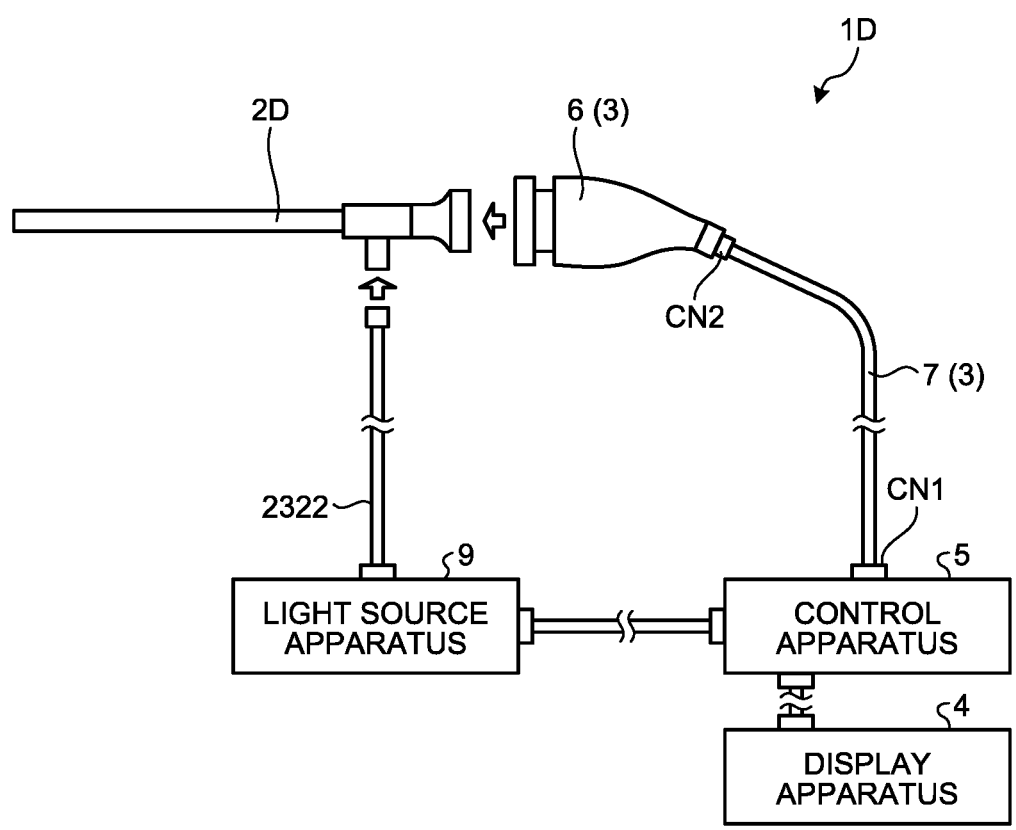
FIG. 13 is a diagram of a modification of the first to the fourth embodiments.

FIG. 13 is a diagram of a modification of the first to the fourth embodiments.

Although the camera heads 6 and 6C are provided detachably relative to the resectoscope 2 for the urinary organs, for example, in the first to the fourth embodiments, this is not limiting; the camera head 6 may be provided detachably relative to an endoscope 2D for the digestive organs, for example, as illustrated in FIG. 13.

The endoscope 2D includes a rigid endoscope. Thus, the endoscope 2D is rigid or at least partly flexible, has an elongated shape, and is inserted into a living body. This endoscope 2D is provided with an optical system that includes one or a plurality of lenses and collects the subject image SI. Light supplied from a light source apparatus 9 (FIG. 13) to the light guide 2322 is emitted from the distal end of the endoscope 2D and is applied to the inside of the living body. The light (the subject image SI) applied to the inside of the living body and reflected by the inside of the living body is collected by the optical system within the endoscope 2D. The camera head 6 captures the subject image SI collected by the optical system within the endoscope 2D.

The endoscope 2D may be a flexible endoscope, not limited to the rigid endoscope.

In the first to the fourth embodiments and the modification thereof (FIG. 13), at least part of the functions of the image processing units 52, 52A, and 52C and the controllers 54, 54B, and 54C may be provided outside the control apparatuses 5 and 5A to 5C (the camera heads 6 and 6C, the connectors CN1 and CN2, or the like).

In the first to the fourth embodiments and the modification thereof (FIG. 13), the endoscopes 1 and 1A to 1D may each be an endoscope that is used in the industrial field for observing the inside of subjects such as mechanical structures.

In the first to the fourth embodiments and the modification thereof (FIG. 13), the following configuration may be used.

The camera heads 6 and 6C output the pixel signals read from the respective pixels of the whole pixel area WPA of the imaging element 651 (the captured image CI0) as the image signal (the RAW signal) to the control apparatuses 5 and 5A to 5C via the cable 7. The control apparatuses 5 and 5A to 5C cut an area corresponding to the specified pixel area SPA or the image SI' of the subject image out of the captured image CI0 and executes the composite image generation processing described in the first to the fourth embodiments.

In the first to the fourth embodiments and the modification thereof (FIG. 13), the reading starting position PS and the reading ending position PE (the specified pixel area SPA) may be changeable in accordance with operations on the operating unit 8 and/or the input unit 55 by the user such as a doctor.

Although the specified pixel area SPA is the area obtained by removing the right and left areas of the subject image SI from the whole pixel area WPA in the first to the fourth embodiments and the modification thereof (FIG. 13), this is not limiting; the specified pixel area SPA may be an area obtained by removing the areas above and below the subject image SI therefrom.

Although in the imaging element 651 the pixel signals are read from the respective pixels in the whole pixel area WPA in the fourth embodiment and the modification thereof (FIG. 13), this is not limiting; the pixel signals may be read from only respective pixels in an area that is smaller than the whole pixel area WPA and contains the entire subject image SI.

Although the first image cutting-out unit 68 cuts the image SI' of the subject image out of the captured image CI0 in the fourth embodiment and the modification thereof (FIG. 13), this is not limiting; a rectangular area containing the entire subject image SI may be cut out of the captured image CI0, for example.

In the endoscope apparatus according to the present disclosure, the imaging apparatus outputs the pixel signals of the respective pixels in the specified pixel area, in the whole pixel area of the imaging element, that is smaller than the whole pixel area and contains the entire subject image as the image signal to the control apparatus via the signal transmission path. Thus, compared with outputting the pixel signals from the respective pixels in the whole pixel area of the imaging element as the image signal from the imaging apparatus to the control apparatus, the amount of information of the image signal output from the imaging apparatus to the control apparatus may be reduced while containing the information on the subject image used for observation.

Consequently, the endoscope apparatus according to the present disclosure produces an effect of making it possible to reduce the amount of information of the image signal and reduce the signal transmission path in size owing to a reduced number of transmission paths, for example.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An endoscope apparatus comprising:
an imaging apparatus that includes an imaging element configured to capture a subject image of inside of a subject, the imaging apparatus outputting an image signal obtained by capturing the subject image by the imaging element;
a control apparatus configured to process the image signal to generate a video signal for display; and
a signal transmission path configured to transmit the image signal from the imaging apparatus to the control apparatus,
wherein the imaging apparatus outputs, as the image signal, pixel signals of first respective pixels in a specified pixel area out of a whole pixel area of the imaging element, the specified pixel area being smaller than the whole pixel area and containing the entire subject image, and wherein the output pixel signals are only from the first respective pixels in the specified pixel area of the imaging element,
wherein the control apparatus includes an edge detector configured to execute mask edge detection processing that detects boundary points between the subject image contained in a captured image and a masked area other than the subject image based on a luminance signal of each pixel in the captured image based on the image signal, and wherein a processor of the control apparatus is configured to:

cut out an image of the subject image surrounded by the boundary points detected by the edge detector in the captured image; and generate a composite image in which the subject image is superimposed onto a background image which is a black level image having a size corresponding to a size of a display on which the composite image is to be displayed.

2. The endoscope apparatus according to claim 1, wherein the pixel signals are read from only the first respective pixels in the specified pixel area of the imaging element.

3. The endoscope apparatus according to claim 1, wherein the imaging apparatus outputs the pixel signals of the first respective pixels in the specified pixel area from among second pixel signals read from second pixels in the whole pixel area outside the specified pixel area.

4. The endoscope apparatus according to claim 1, wherein:

the control apparatus includes an imaging controller configured to control operation of the imaging apparatus, and the imaging controller sets the specified pixel area based on an area of a subject image surrounded by the boundary points detected by the edge detector in the captured image and outputs the pixel signals of the respective pixels in the specified pixel area as the image signal from the imaging apparatus.

* * * * *